(12) United States Patent
Egawa (10) Patent No.: US 12,025,760 B2
(45) Date of Patent: Jul. 2, 2024

(54) RADIATION IMAGING APPARATUS AND RADIATION IMAGING SYSTEM

(71) Applicant: CANON KABUSHIKI KAISHA, Tokyo (JP)

(72) Inventor: Riku Egawa, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/694,832

(22) Filed: Mar. 15, 2022

(65) Prior Publication Data
US 2022/0299664 A1    Sep. 22, 2022

(30) Foreign Application Priority Data

Mar. 16, 2021 (JP) ................................. 2021-042179
Feb. 24, 2022 (JP) ................................. 2022-026889

(51) Int. Cl.
| | |
|---|---|
| *G01T 1/24* | (2006.01) |
| *A61B 6/00* | (2024.01) |
| *A61B 6/42* | (2024.01) |
| *G01T 1/20* | (2006.01) |

(52) U.S. Cl.
CPC ............ *G01T 1/244* (2013.01); *A61B 6/4283* (2013.01); *A61B 6/4405* (2013.01); *G01T 1/20188* (2020.05); *G01T 1/2019* (2020.05)

(58) Field of Classification Search
CPC ... G01T 1/244; G01T 1/20188; G01T 1/2019; A61B 6/4283; A61B 6/4405
See application file for complete search history.

(56) References Cited

U.S. PATENT DOCUMENTS

| | | | | |
|---|---|---|---|---|
| 2004/0211909 A1* | 10/2004 | Watanabe | ............... | G03B 42/02 |
| | | | | 250/370.11 |
| 2004/0245474 A1* | 12/2004 | Vieux | ................... | G01T 1/2002 |
| | | | | 250/370.11 |
| 2012/0074331 A1* | 3/2012 | Koyanagi | .............. | G03B 42/04 |
| | | | | 250/394 |

FOREIGN PATENT DOCUMENTS

| | | |
|---|---|---|
| JP | 2002-214352 A | 7/2002 |
| JP | 2003-57352 A | 2/2003 |
| JP | 2010-276687 A | 12/2010 |
| JP | 2012-202735 A | 10/2012 |
| JP | 2012-211866 A | 11/2012 |

\* cited by examiner

*Primary Examiner* — David P Porta
*Assistant Examiner* — Casey Bryant
(74) *Attorney, Agent, or Firm* — VENABLE LLP

(57) ABSTRACT

Disclosed apparatus comprises: a radiation detection panel in a housing, for detecting incident radiation as an electrical signal related to a radiation image; a support base in the housing and located on a side opposite to a radiation incident surface, for supporting the radiation detection panel from a back surface side; an internal structure in the housing and disposed on the back side surface of the support base; and fixing members in the housing, for fixing the internal structure to the support base, the difference in the radiation shielding efficiency between at least one of the fixing members and the support base is less than 50%, and when viewed from a radiation incident direction, a sheet like member having a radiation shielding efficiency of 50% or more is not arranged on a region on the back surface side of the radiation detection panel overlapping with the fixing member.

11 Claims, 5 Drawing Sheets

FIG. 5

RADIATION IMAGING APPARATUS AND RADIATION IMAGING SYSTEM

BACKGROUND OF THE INVENTION

Field of the Invention

The present invention relates to a radiation imaging apparatus and a radiation imaging system.

Description of the Related Art

In recent years, a digital radiation imaging apparatus for acquiring a digital image using a semiconductor sensor is widely used for medical image diagnosis and nondestructive inspection.

In addition, a portable type radiation imaging apparatus in which a digital radiation imaging apparatus is miniaturized and reduced in weight is used for imaging in a general hospital room, outdoors, etc. (refer to the specification of U.S. Patent Application Publication No. 2004/0211909).

When radiation imaging is performed, irradiation of radiation may be performed with the irradiated region made larger than the outer shape of imaging apparatus. In this case, the irradiated radiation without being irradiated with the imaging apparatus is scattered by a structure such as a wall surface or a floor located on the back side of imaging apparatus, and enters the interior of imaging apparatus from the back side thereof, and becomes an input to the imaging element. Scattered radiation incident due to such scattering from the back side of imaging apparatus is reflected in the image as a difference in radiation shielding efficiency due to a member or the like inside the imaging apparatus, and can be an artifact leading to misdiagnosis.

As an example of this countermeasure, Japanese Patent Application Laid-Open No. 2002-214352 discloses that a radiation shield is disposed so as to cover the entire imaging element region in order to shield the incidence of scattered radiation to the imaging element, and a metal plate material having high radiation shielding property such as lead (Pb) is used as the radiation shield. In such a metal plate material, it is generally known that the radiation shielding property is lowered when the surface density is reduced, and in order to have sufficient radiation shielding property, it is necessary to arrange a metal plate material having a high specific gravity or a large plate thickness as a radiation shielding body. On the other hand, this increases the total weight of the radiation imaging apparatus, and the portability of the portable radiation imaging apparatus is impaired.

As a method for reducing the weight of the apparatus and suppressing the artifact due to scattered radiation, there are a method in which a radiation shielding body is made detachably attached as described in Japanese Patent Application Laid-Open No. 2003-57352 and a method in which a part of a substrate supporting an imaging element has a shielding function as described in Japanese Patent Application Laid-Open No. 2012-211866.

However, the improvement of the portability of the radiation imaging apparatus by eliminating or reducing the weight of the radiation shield and the suppression of the deterioration of the image quality of the radiation image due to scattered radiation are insufficient.

SUMMARY OF THE INVENTION

Disclosure is invented in consideration of the background described above, and it is an object of the present invention to provide a radiation imaging apparatus capable of suppressing deterioration in image quality of a radiation image without impairing portability.

Disclosed is a radiation imaging apparatus comprising: a radiation detection panel which is included in a housing, configured to detect incident radiation as an electrical signal related to a radiation image; a support base which is included in the housing, configured to support the radiation detection panel on a back surface side which is a side opposite to a radiation incident surface side; an internal structure which is included in the housing and is disposed on the back surface side of the support base; and a plurality of fixing members which are included in the housing, configured to fix the internal structure to the support base, wherein the difference in the radiation shielding efficiency between at least one of the plurality of fixing members and the support base is less than 50%, and in a plan view viewed from a radiation incident direction, a sheet like member having a radiation shielding efficiency of 50% or more is not arranged on a region on the back surface side of the radiation detection panel which overlaps with the fixing member.

The present disclosure also includes a radiation imaging system having the radiation imaging apparatus described above and a radiation irradiation apparatus for irradiating the radiation.

According to one aspect of the disclosure, it is possible to suppress deterioration in image quality of a radiation image without impairing portability of the radiation imaging apparatus.

Further features of the present invention will become apparent from the following description of exemplary embodiments with reference to the attached drawings.

DESCRIPTION OF THE EMBODIMENTS

Embodiments of the present disclosure will be described below with reference to the drawings. It should be noted that the dimensions and structures of the various structures in the embodiments of the present disclosure described below are not limited to those shown in the description and drawings. Although it is preferable to use X-rays as the radiation in the present disclosure, it is not limited to the X-rays, and alpha rays, beta rays, gamma rays, particle rays, cosmic rays, and the like are included in the radiation in the present disclosure.

First Embodiment

Figure 1:
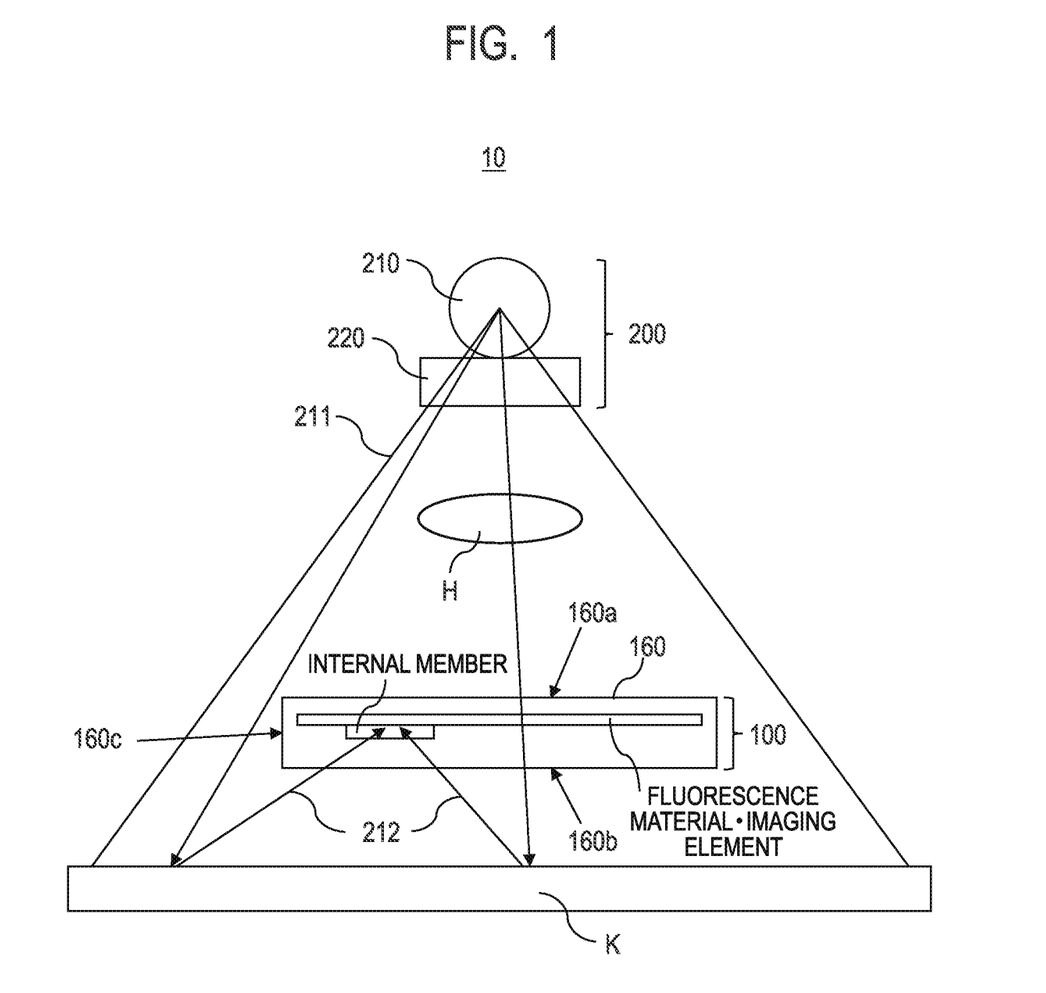
FIG. 1 is a schematic diagram showing an example of a schematic configuration of a radiation imaging system according to the first embodiment.

FIG. 1 is a schematic diagram showing an example of a schematic configuration of a radiation imaging system 10 according to a first embodiment of the present disclosure. The radiation imaging system 10 comprises a radiation imaging apparatus 100 and a radiation irradiation apparatus 200, and may be used particularly for medical purposes.

The radiation irradiation apparatus 200 irradiates the object H with radiation 211. The radiation irradiation apparatus 200 includes a radiation tube 210 which is an X-ray generating unit generating radiation 211, and a collimator 220 defining a beam spread angle of the radiation 211 generated by the radiation tube 210.

The radiation imaging apparatus 100 is composed of, for example, a flat panel detector (FPD). In the example shown in FIG. 1, the housing 160 of the radiation imaging apparatus 100 is composed of a radiation incident surface 160a into which the radiation 211 enters, a back surface 160b located on the side opposite to the radiation incident surface 160a, and a side surface 160c connecting the radiation incident surface 160a and the back surface 160b at ends. In addition, a fluorescence material and an imaging element, and a member or the like disposed on the back surface 160b of the fluorescence material and the imaging element housed in the housing 160 are shown in FIG. 1.

Next, the scattered radiation referred to in the problem to be solved by the present disclosure will be described with reference to FIG. 1.

The radiation 211 irradiated from the radiation irradiation apparatus 200 enters the inside of the housing 160 of the radiation imaging apparatus 100, is absorbed by the fluorescence material, and is converted into visible light. The visible light generated by the fluorescence material is received by the imaging element distributed in two dimensions, and an electric signal (image signal) relating to the radiation image corresponding to the two-dimensional distribution (dose distribution) of the radiation dose is generated in the imaging element.

On the other hand, some of the radiation 211 irradiated from the radiation irradiation apparatus 200 passes through the radiation imaging apparatus 100 without being absorbed, and some passes through the outside without passing through the radiation imaging apparatus 100. Such passing radiation 211 are scattered by a structure K such as a wall surface or a floor located on the side of the back surface 160b of the radiation imaging apparatus 100, and may enter from the side of the back surface 160b of the radiation imaging apparatus 100. Here, the radiation 211 incident from the side of the back surface 160b of the radiation imaging apparatus 100 by scattering is referred to as scattered radiation 212. Then, the scattered radiation 212 is shielded by a member or the like disposed on the back surface 160b of the fluorescence material and the imaging element, so that the pixel value of the shielded portion becomes low, and the difference in the shading appears as a ghost image on the radiation image. Therefore, as the number and ratio of scattered radiation 212 incident from the side of the back surface 160b of the radiation imaging apparatus 100 increases, the amount of the ghost image increases, and the image quality degradation of the radiation image increases.

The scattered radiation 212 incident from the side of the back surface 160b of the radiation imaging apparatus 100 depends on the imaging condition such as the imaging site of an object H, and the tube voltage of a radiation tube 210, and on the imaging environment such as the size of an aperture of a collimator 220, the SID which is the distance from the radiation tube 210 to the radiation imaging apparatus 100, and the distance from the radiation imaging apparatus 100 to the structure K. For example, the higher the tube voltage in the radiation tube 210, the greater the number of radiation 211 penetrating the interior of the radiation imaging apparatus 100, and consequently the greater the number of scattered radiation 212 incident from the side of the back surface 160b of the radiation imaging apparatus 100. Further, for example, in the thick region of the object H, that is, in the region where the dose of the radiation 211 is small, the ratio of the scattered radiation 212 incident from the side of the back surface 160b of the radiation imaging apparatus 100 increases, and as a result, the ghost image becomes easy to see. Also, depending on the size of the aperture of the collimator 220 and the SID, for example, the number of radiation 211 passing outside the radiation imaging apparatus 100 may increase, and consequently the number of scattered radiation 212 incident from the side of the back surface 160b of the radiation imaging apparatus 100 may also increase. Regarding the distance between the radiation imaging apparatus 100 and the structure K, the number of scattered radiation 212 incident from the side of the back surface 160b of the radiation imaging apparatus 100 becomes a peak at a certain distance, and the number of scattered radiation 212 decreases as the distance approaches the structure K, and the number of scattered radiation 212 decreases as the distance goes further.

Next, the radiation shielding efficiency (X-ray shielding efficiency when X-rays are applied as radiation) will be described.

The radiation shielding efficiency (X-ray shielding efficiency) in this embodiment is taken into consideration when the tube voltage of the radiation tube 210 is 120 kV or less. The radiation shielding efficiency (X-ray shielding efficiency) of an arbitrary object is expressed by the following equation (1), where I is the energy obtained by measuring the radiation 211 (X-ray) irradiated by providing a certain tube voltage at an arbitrary position within a range of 0.5 m to 2 m from the radiation tube 210, and I' is the energy obtained by measuring the radiation 211 (X-ray) irradiated by providing the same tube voltage and transmitted through the object at the same position.

$$\text{Radiation shielding efficiency} = (1 - I'/I) \times 100 [\%] \qquad (1)$$

Next, the internal configuration of the radiation imaging apparatus 100 according to the first embodiment will be described.

Figure 2:
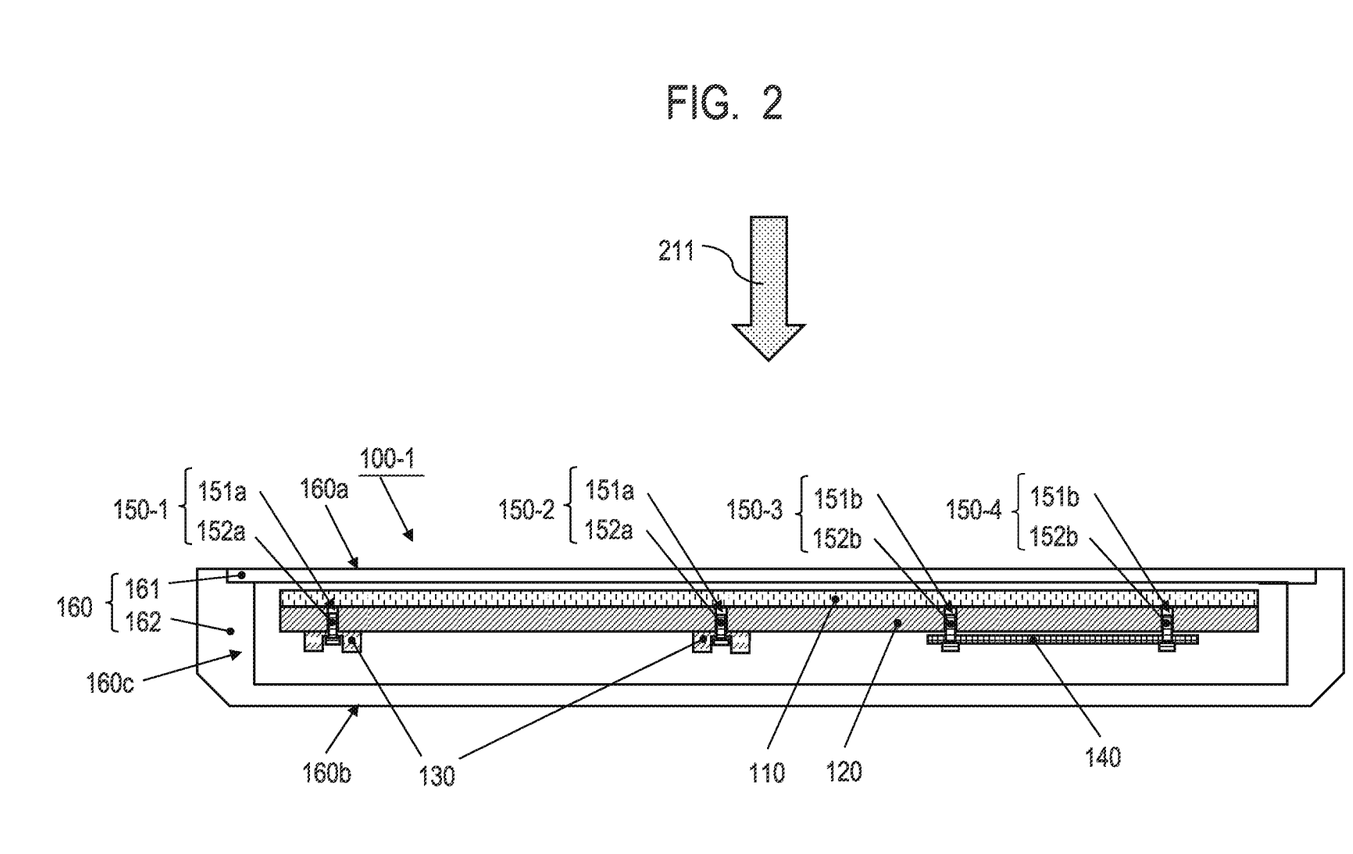
FIG. 2 is a cross section diagram showing an example of the internal configuration of the radiation imaging apparatus according to the first embodiment.

FIG. 2 is a cross section diagram showing an example of the internal configuration of the radiation imaging apparatus 100 according to the first embodiment of the present disclosure. Specifically, FIG. 2 is a view taken in the same direction as the radiation imaging apparatus 100 shown in FIG. 1. In the following description, the radiation imaging apparatus 100 according to the first embodiment shown in FIG. 2 is described as "radiation imaging apparatus 100-1". In FIG. 2, the same constituent elements as those shown in FIG. 1 are denoted by the same reference numerals.

As shown in FIG. 2, the radiation imaging apparatus 100-1 includes a radiation detection panel 110, a support base 120, an internal component 130, an electric substrate 140, a fixing member 150, and a housing 160.

The radiation detection panel 110 is included in the housing 160 and detects incident radiation 211 as an electric signal (image signal) related to a radiation image. The radiation detection panel 110 includes a fluorescence material and an imaging element shown in FIG. 1.

The support base 120 is included in the housing 160, and is a base for supporting the radiation detection panel 110 from the side of the back surface 160b located on the side opposite to the radiation incident surface 160a where the radiation 211 enters the housing 160.

The internal component 130 is a component included in the housing 160 and disposed on the side of the back surface 160b of the support base 120. For example, the internal component 130 is a component (for example, a component for fitting to a member joined to the housing 160) for fixing the radiation detection panel 110 and the support base 120 to the housing 160. The electric substrate 140 is included in the housing 160 and disposed on the side of the back surface 160b of the support base 120. For example, the electric substrate 140 is an electric substrate for supplying power to the radiation detection panel 110 or for processing an electric signal (image signal) related to a radiation image obtained by the radiation detection panel 110. These internal components 130 and the electric substrate 140 preferably have a radiation shielding efficiency of less than 50% as defined by equation (1). In the present embodiment, the internal component 130 and the electric substrate 140 are components that are included in the housing 160 and correspond to "internal structures" disposed on the side of back surface 160b for the support base 120.

The fixing members 150-1 to 150-4 are a plurality of fixing members included in the housing 160 and fixing the internal components 130 and the electric substrate 140, which are the internal structures as described above, to the support base 120. Of the plurality of fixing members 150-1 to 150-4, the fixing member 150-1 and the fixing member 150-2 are members for fixing the internal components 130 arranged corresponding to each other to the support base 120, and each member has a screw structure consisting of a female screw 151a and a male screw 152a. Among the plurality of fixing members 150-1 to 150-4, the fixing member 150-3 and the fixing member 150-4 are members for fixing the electric substrate 140 to the support base 120, and each member has a screw structure consisting of a female screw 151a and a male screw 152a. In the example shown in FIG. 2, the plurality of fixing members 150-1 to 150-4 are members disposed inside the support base 120.

The housing 160 is a housing of the radiation imaging apparatus 100-1 including the radiation detection panel 110, the support base 120, the internal component 130, the electric substrate 140, and the fixing member 150. In the example shown in FIG. 2, the housing 160 comprises a front cover portion 161 having the radiation incident surface 160a and a back cover portion 162 having the back surface 160b and the side surface 160c. In this embodiment, the housing 160 is not limited to the housing including the front cover portion 161 and the back cover portion 162 shown in FIG. 2. For example, the back cover portion 162 may be divided into a back cover portion having the back surface 160b and a frame portion having the side surface 160c. The front cover portion 161 having the radiation incident surface 160a is made of a material having a radiation absorptivity lower than that of the back cover portion 162 in order to make the radiation 211 incident on the radiation detection panel 110. Further, the front cover portion 161 having the radiation incident surface 160a is preferably made of a material which is light in weight and can secure a certain strength against impact or the like. For example, a resin material, CFRP (carbon fiber reinforced plastic), or the like is used as a constituent material of the front cover portion 161 having the radiation incident surface 160a. The back cover portion 162 is preferably made of a material having a low specific gravity such as magnesium, aluminum, or CFRP, for example, in order to secure strength against falling, impact, or the like, and to reduce the load during transportation.

In the radiation imaging apparatus 100-1 according to the present embodiment, as shown in FIG. 2, a sheet like member having a radiation shielding efficiency of 50% or more as defined by the above equation (1) is not arranged on the back surface 160b side of the radiation detection panel 110 in a plan view as viewed from the radiation incident direction. Further, the sheet like member is not arranged at least in the region overlapping the fixing members 150-1 to 150-4.

Next, the support base 120 and the fixing member 150 shown in FIG. 2 will be described in detail.

The support base 120 and the fixing member 150 are preferably made of a material having a relatively high specific rigidity, for example, an alloy containing at least one of Al and Mg or a composite material containing carbon fibers. The fixing member 150 includes one or both of the female screws 151a and 151b and the male screws 152a and 152b. In the example shown in FIG. 2, the female screw 151 of the fixing member 150 is integrated with the support base 120, but the present embodiment is not limited thereto, and may be separated from the support base 120, for example. In such case, in the radiation imaging apparatus 100-1 according to the present embodiment, the difference in the radiation shielding efficiency between the support base 120 and at least one of the fixing members 150-1 to 150-4 of the plurality of fixing members 150 is less than 50%.

For example, when the support base 120 is an alloy of Al or Mg having a thickness of 1 mm to 3 mm, all the fixing members 150-1 to 150-4 are preferably formed of an alloy of Al or Mg having a thickness of 6 mm or less with respect to the incident direction of the radiation 211. In this case, it is preferable that all the female screws 151 are formed of an alloy of Al or Mg whose thickness is 6 mm or less with respect to the incident direction of the radiation 211. When the support base 120 and the fixing members 150-1 to 150-4 are made of the same material, the thickness of the fixing members 150-1 to 150-4 is preferably in the range of 1 to 6 times the thickness of the support base 120. Alternatively, it is preferable that the female screw 151 disposed near the center of the image taken region of the radiation imaging apparatus 100-1 is formed of an alloy containing Al or Mg with a thickness of 6 mm or less. This is because the thickness of the object H tends to increase in the vicinity of the center of the radiation imaging apparatus 100-1, and the dose of the radiation 211 that passes through the object H and reaches the radiation detection panel 110 decreases with respect to the dose of the scattered radiation 212, so that the influence of the scattered radiation 212 on the radiation image increases. For example, when the support base 120 is formed of a resin material such as CFRP or GFRP, all the fixing members 150-1 to 150-4 are preferably formed of a resin material.

As described above, in the radiation imaging apparatus 100-1 according to the first embodiment, the difference in radiation shielding efficiency between at least one of the fixing members 150-1 to 150-4 and the support base 120 is less than 50%, and a sheet like member having a radiation shielding efficiency of 50% or more is not arranged on the side of the back surface 160b for the radiation detection panel 110.

According to this configuration, since no sheet like member having a radiation shielding efficiency of 50% or more (high specific gravity or large plate thickness) is disposed, the weight increase can be suppressed, so that the portability of the radiation imaging apparatus is not impaired, and since the difference in the radiation shielding efficiency between at least one of fixing members 150-1 to 150-4 and the support base 120 is less than 50%, deterioration in the image quality of the radiation image due to scattered radiation can be suppressed. As a result, a highly reliable radiation image can be provided.

Second Embodiment

In the description of the second embodiment, description of matters common to the first embodiment will be omitted, and matters different from the first embodiment will be mainly described.

The schematic configuration of the radiation imaging system according to the second embodiment is the same as that of the radiation imaging system 10 according to the first embodiment shown in FIG. 1.

Next, the internal configuration of the radiation imaging apparatus 100 according to the second embodiment will be described.

Figure 3:
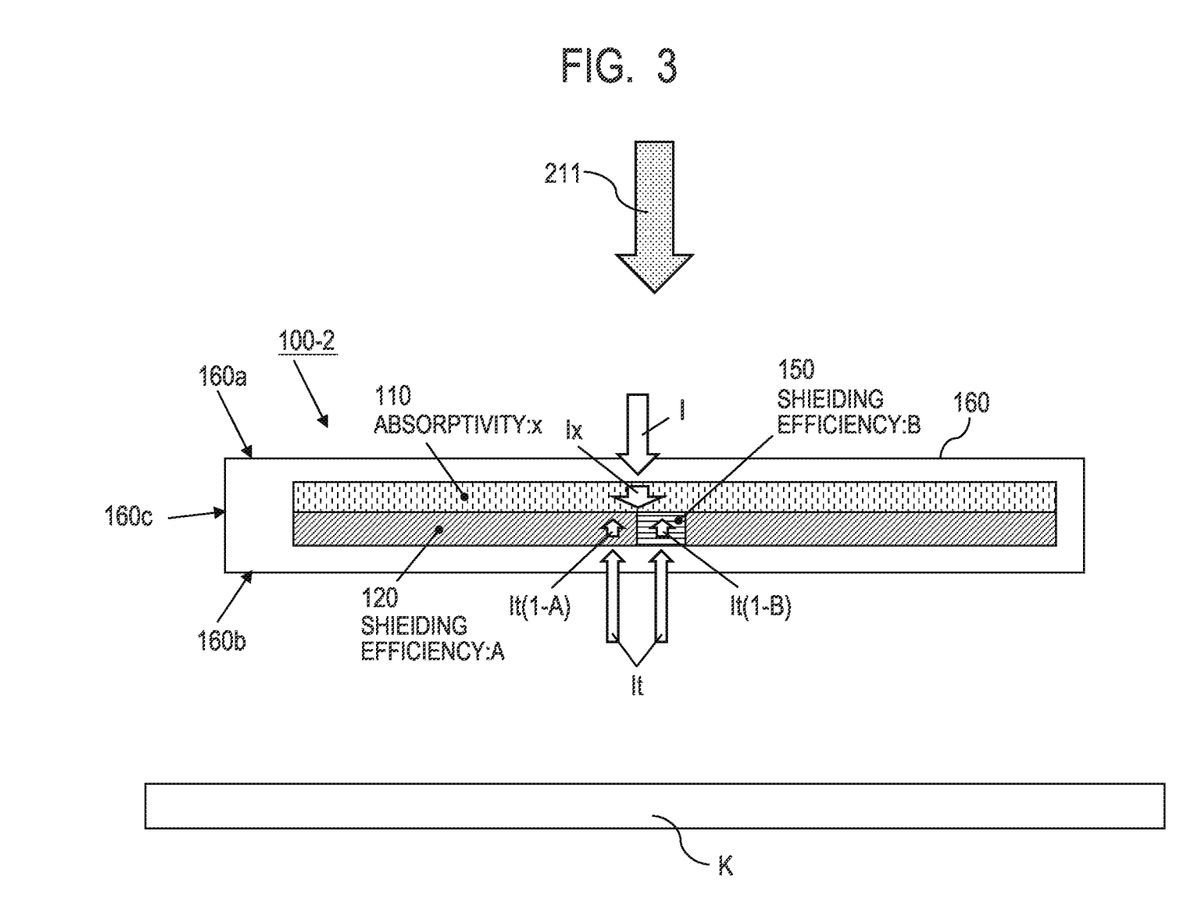
FIG. 3 is a cross section diagram showing an example of the internal configuration of the radiation imaging apparatus according to the second embodiment.

FIG. 3 is a cross section diagram showing an example of the internal configuration of the radiation imaging apparatus 100 according to the second embodiment of the present invention. Specifically, FIG. 3 is a view taken in the same direction as the radiation imaging apparatus 100 shown in FIG. 1. In the following description, the radiation imaging apparatus 100 according to the second embodiment shown in FIG. 3 is described as "radiation imaging apparatus 100-2". In FIG. 3, the same components as those shown in FIGS. 1 and 2 are denoted by the same reference numerals. Further, in FIG. 3, the fixing member 150 of one of the plurality of fixing members 150-1 to 150-4 shown in FIG. 2 is illustrated as a representative.

In the second embodiment, unlike the first embodiment described above, the radiation absorptivity of the radiation detection panel 110 is also considered. In the radiation imaging apparatus 100-2 according to the second embodiment, a ratio of the radiation absorptivity in the radiation detection panel 110 of the radiation 211 directly incident on the radiation detection panel 110 to the difference in the radiation shielding efficiency between the support base 120 and at least one of the fixing members 150 of the plurality of fixing members (150-1 to 150-4) for the scattered radiation 212 is less than 5%. This relationship will be described in detail below with reference to FIG. 3.

As shown in FIG. 3, the radiation absorptivity (X-ray absorptivity) of the radiation detection panel 110 is represented by x, the radiation shielding efficiency (X-ray shielding efficiency) of the support base 120 is represented by A, and the radiation shielding efficiency (X-ray shielding efficiency) of the fixing member 150 is represented by B. Further, the energy of the scattered radiation (scattered X-ray) 212 is represented as It by using the attenuation coefficient t, since the energy I of the irradiated radiation (X-ray) 211 is scattered by the structure K located on the side of the back surface 160b of the radiation imaging apparatus 100.

In view of the above, the energy of the radiation shown in FIG. 3 is expressed as follows.

Energy of the radiation 211 absorbed by the radiation detection panel 110: Ix

Energy of the scattered radiation 212 that passes through the support base 120 and reaches the radiation detection panel 110: It (1−A)

Energy of the scattered radiation 212 that passes through the fixing member 150 and reaches the radiation detection panel 110: It (1−B)

As described above, in the present embodiment, the ration of the difference in the radiation shielding efficiency (X-ray shielding efficiency) between the fixing member 150 and the support base 120 with respect to the scattered radiation (scattered X-ray) 212 with respect to the radiation absorptivity (X-ray absorptivity) x of the radiation (X-ray) 211 directly incident on the radiation detection panel 110 in the radiation detection panel 110 has the following relation (2).

$$(It(1-A)-It(1-B))/Ix=(t(B-A))/x<5\%  \quad (2)$$

Further, in the present embodiment, the attenuation coefficient t is considered under the condition that the amount of scattered radiation 212 incident on the radiation imaging apparatus 100-2 becomes relatively large. Specifically, for example, the tube voltage of the radiation tube 210 is 120 kV or less, the distance from the radiation tube 210 to the radiation imaging apparatus 100-2 is 2 m or less, and the distance from the radiation imaging apparatus 100-2 to the structure K is 50 cm or less.

The fluorescence material included in the radiation detection panel 110 according to the present embodiment includes, for example, a metal oxide such as CsI, and $Gd_2O_2S$, as a component, and has a characteristic of converting radiation into visible light, and its film thickness is in the range of 200 μm to 600 μm.

In the radiation imaging apparatus 100-2 according to the second embodiment, similarly to the radiation imaging apparatus 100-1 according to the first embodiment, deterioration in image quality of the radiation image due to scattered radiation can be suppressed without impairing portability of the radiation imaging apparatus. As a result, a highly reliable radiation image can be provided.

Third Embodiment

In the description of the third embodiment, the description of matters common to the first and second embodiments will be omitted, and matters different from the first and second embodiments will be mainly described.

The schematic configuration of the radiation imaging system according to the third embodiment is the same as that of the radiation imaging system 10 according to the first embodiment shown in FIG. 1.

Next, the internal configuration of the radiation imaging apparatus 100 according to the third embodiment will be described.

Figure 4:
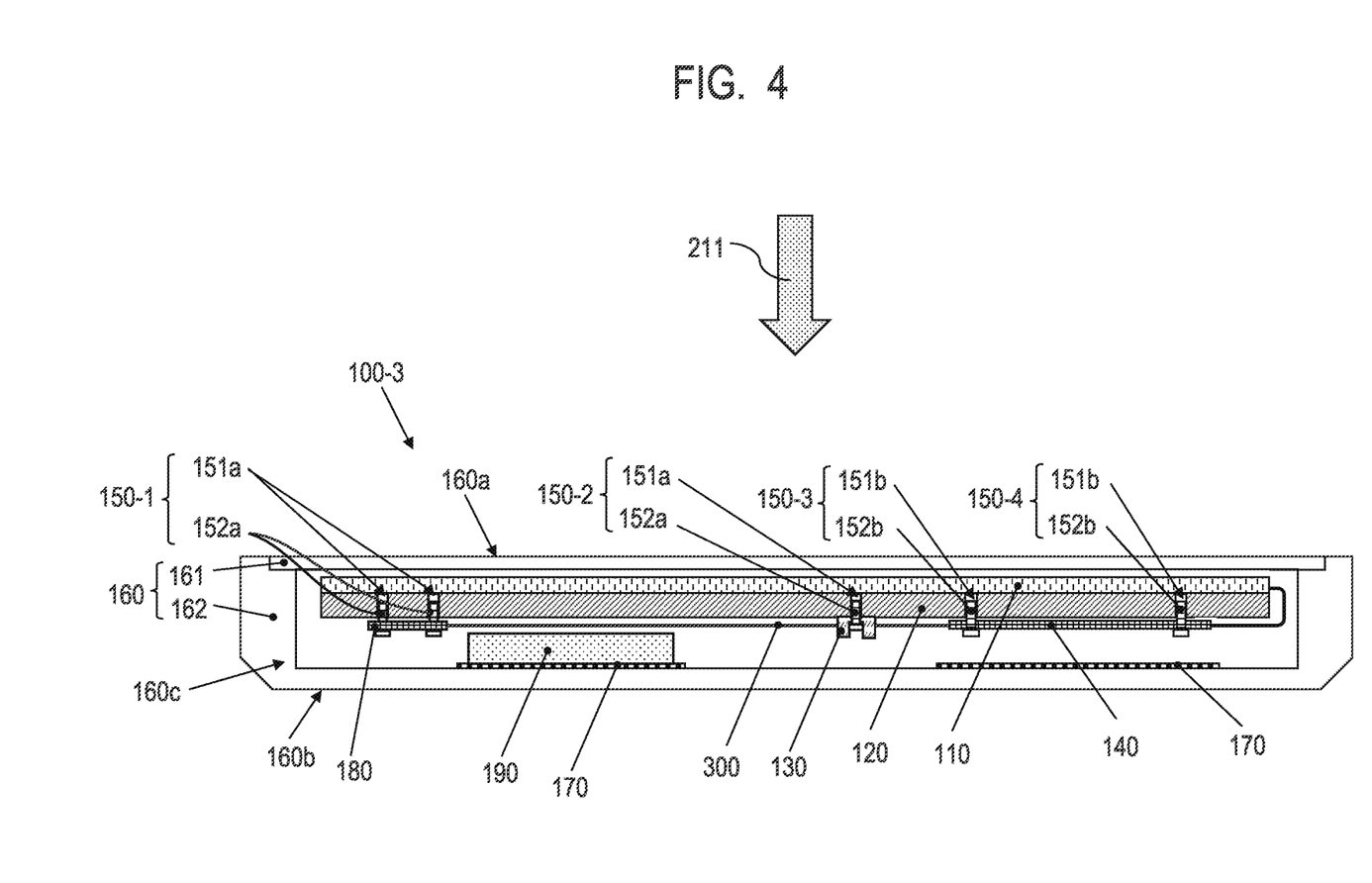
FIG. 4 is a cross section diagram showing an example of the internal configuration of the radiation imaging apparatus according to the third embodiment.
Figure 5:
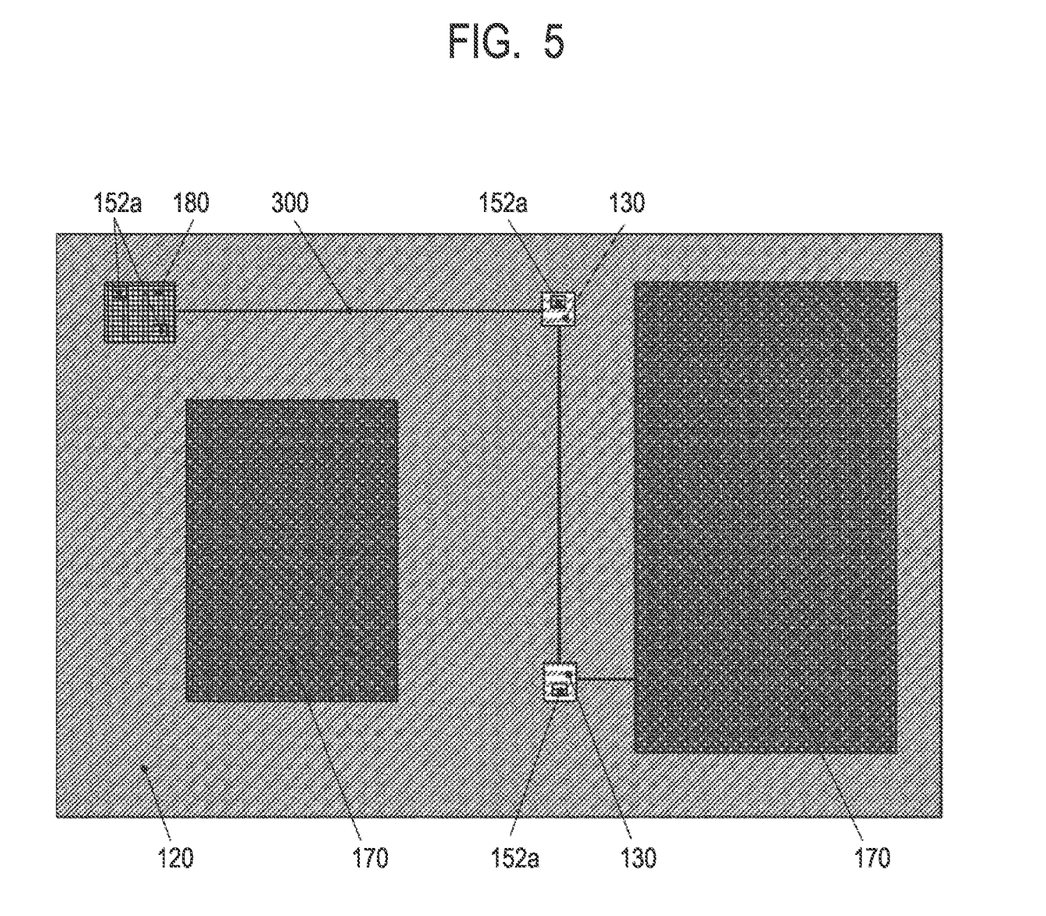
FIG. 5 is a plan view showing an example of the internal configuration of the radiation imaging apparatus according to the third embodiment in a plan view.

FIG. 4 is a cross section diagram showing an example of the internal configuration of the radiation imaging apparatus 100 according to the third embodiment of the present invention. Specifically, FIG. 4 is a view taken in the same direction as the radiation imaging apparatus 100 shown in FIG. 1. FIG. 5 is a perspective plan view of the housing 160 (from the side opposite to the incident side) in a plan view viewed from the radiation incident direction. In the following description, the radiation imaging apparatus 100 according to the third embodiment shown in FIG. 4 is described as "radiation imaging apparatus 100-3". In FIGS. 4 and 5, the same components as those shown in FIGS. 1 to 3 are denoted by the same reference numerals.

In the radiation imaging apparatus 100-3 according to the third embodiment shown in FIG. 4, a sheet like radiation shielding member (hereinafter, the sheet like member) 170 is additionally disposed on the side of the back surface 160b of the radiation detection panel 110 in comparison with the radiation imaging apparatus 100-1 according to the first embodiment shown in FIG. 2. The sheet like member 170 is preferably a weak shielding member of less than 50% of shielding efficiency of radiation transmitted through the radiation detection panel 110, but the radiation shielding efficiency may be 50% or more. The sheet like member 170 is made of a material containing a metal other than lead.

The housing 160 includes a battery 190 for supplying electric power to each part such as the radiation detection panel 110 and the electric substrate 104, a charging circuit 180 for rectifying a current supplied from the outside and charging the battery 190 with a predetermined voltage, and wiring 300 connecting the charging circuit 180 and the electric substrate 140. The internal component 130 includes a clamp for fixing the wiring 300 to the support base 120 at a predetermined position. In FIG. 4, the battery 190 is completely included in the housing 160, but those are not limited by such arrangement, and the battery may be detachably mounted from an opening provided in the back cover portion 162. The sheet like member 170 is arranged in a substantially rectangular shape so as to completely cover a projection plane to the back surface 160b in a region overlapping both the battery 190 and the electric substrate 140 (including fixing members 150-3 and 150-4 fixing the electric substrate 140 to the support base 160) in a plan view viewed from a radiation incident direction. The sheet like member 170 may be disposed on either one of the projection plane of the battery 190 and the projection plane of the electric substrate 140. Further, the sheet like member 170 may be not substantially rectangular in shape but partially cut out, or may be triangular or round in shape. However, the sheet like member 170 is not arranged on the projection plane of the fixing members 150-1 and 150-2 to the back surface 160b.

The fixing members 151a and 151b are female screws integrated with a support base 120 made of a structural material having relatively high specific rigidity such as an alloy containing Al or Mg or a composite material containing carbon fibers, and the fixing members 152a and 152b are male screws made of an iron-based material. At this time, the difference in the radiation shielding efficiency between the male screw and the support base 120 is preferably less than 50%, but may be 50% or more.

By partially arranging the sheet like member 170, scattered radiation 212 reaching the support base 120, the female screw 151a, the male screw 152a and the battery 190 on the projection plane of the sheet like member 170 can be reduced. As a result, it is possible to partially suppress reflection into the radiation image, and further to suppress deterioration of the electric substrate 140 and the battery 190 due to radiation.

In the radiation imaging apparatus 100-3 according to the third embodiment, similarly to the radiation imaging apparatus 100-1 according to the first embodiment, deterioration in image quality of the radiation image due to scattered radiation can be suppressed without impairing portability of the radiation imaging apparatus. As a result, a highly reliable radiation image can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-042179, filed Mar. 16, 2021, and Japanese Patent Application No. 2022-026889, filed Feb. 24, 2022 which are hereby incorporated by reference herein in their entirety.

What is claimed is:

1. A radiation imaging apparatus comprising:
   a radiation detection panel configured to detect incident radiation;
   a support base configured to support the radiation detection panel on a front surface side, provided with a first opening at a position overlapping a part of the radiation detection panel in an incident direction of the radiation;
   an internal structure having a second opening;
   a fixing member configured to be inserted into the first and second openings to fix the internal structure to a back side of the support base; and
   a housing that houses the radiation detection panel, the support base, and the internal structure, has a front section for irradiating the radiation detection panel with radiation, and has a back section that is located on an opposite side of the front section,
   wherein no sheet like radiation shielding member having a radiation shielding efficiency of 50% or more is arranged in an area that overlaps the fixing member when viewed in the radiation incident direction,
   wherein the support base is made of an alloy containing at least one of Al and Mg or a composite material containing carbon fibers, and the fixing member is made of an alloy containing at least one of Al and Mg or a composite material containing carbon fibers so that the difference in radiation shielding efficiency with the support base is less than 50%, and
   wherein the radiation shielding efficiency is calculated when a type of radiation is X-ray, a tube voltage of an X-ray tube bulb is 120 kV or less, and a distance from the X-ray tube bulb is 0.5 m to 2 m.

2. The radiation imaging apparatus according to claim 1, wherein a sheet like radiation shielding member having a radiation shielding efficiency of 50% or more is arranged in another area that does not overlap the fixing member when viewed in the radiation incident direction on the back surface side of the radiation detection panel.

3. The radiation imaging apparatus according to claim 1, wherein a sheet like radiation shielding member having a radiation shielding efficiency of less than 50% is arranged in the area.

4. The radiation imaging apparatus according to claim 2, wherein the internal structure includes an electric substrate for processing the electric signal, and
   the sheet like radiation shielding member having a radiation shielding efficiency of 50% or more overlaps the electric substrate when viewed in the radiation incident direction.

5. The radiation imaging apparatus according to claim 3, wherein the sheet like radiation shielding member has a radiation shielding efficiency less than 50% and
   is made of a material containing a metal other than lead.

6. The radiation imaging apparatus according to claim 1, wherein a ratio of a radiation absorptivity in the radiation detection panel of the radiation directly incident on the radiation detection panel to a difference in the radiation shielding efficiency between the support base and at least one of the fixing members for a scattered radiation which is the radiation incident by scattering, is less than 5%.

7. The radiation imaging apparatus according to claim 1, wherein the fixing member has an inserting portion inserted into the first and second openings.

8. The radiation imaging apparatus according to claim 7, wherein the inserting portion has at least one of a female screw structure and a male screw structure.

9. The radiation imaging apparatus according to claim 8, wherein the fixing member is a male screw.

10. The radiation imaging apparatus according to claim 1, wherein the internal structure includes an internal component for fixing the radiation detection panel and the support base to the housing.

11. A radiation imaging system comprising:
   the radiation imaging apparatus according to claim 1; and
   a radiation irradiation apparatus configured to irradiate the radiation.

* * * * *